Figure 1:
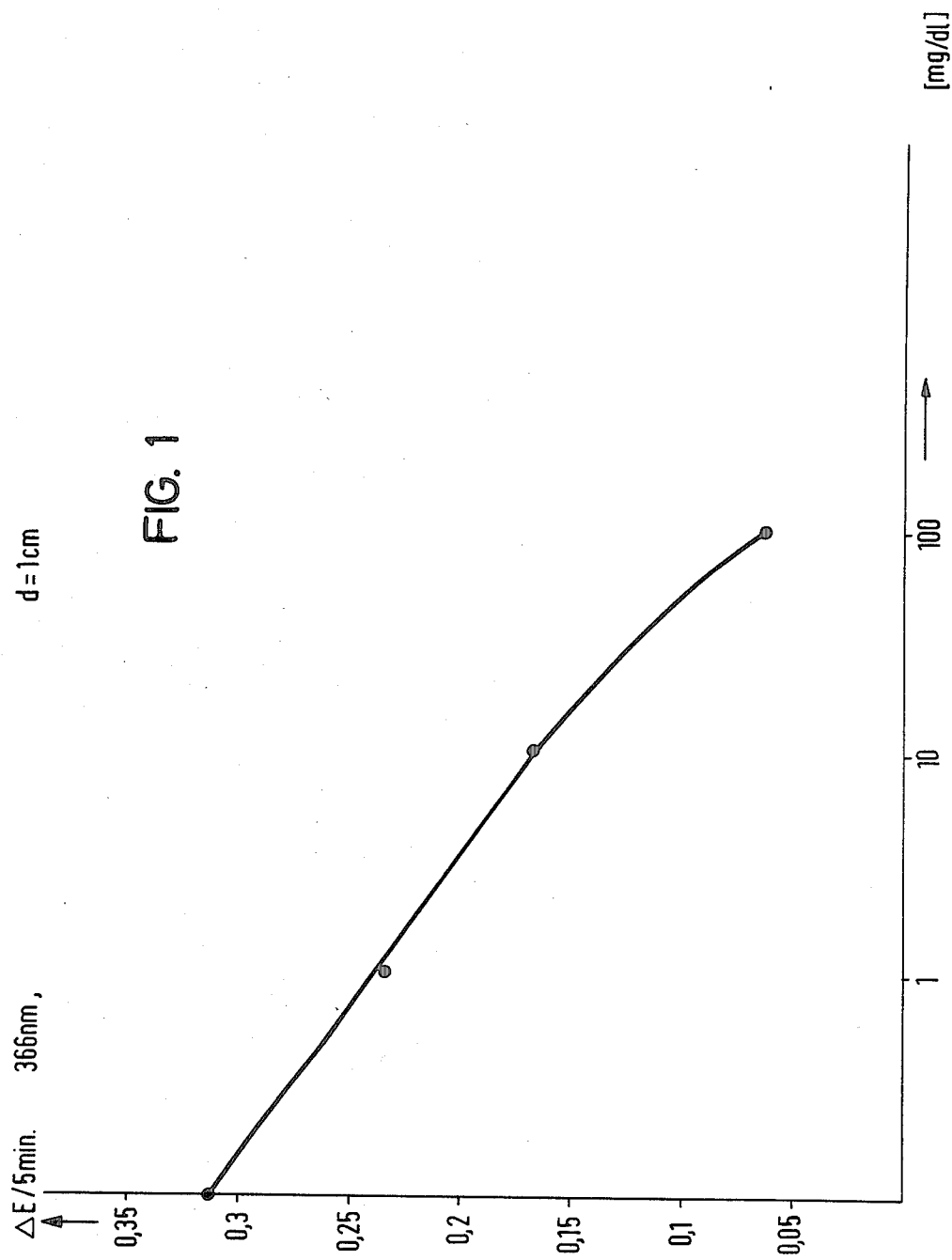

United States Patent [19]

Albert et al.

[11] Patent Number: 4,543,325

[45] Date of Patent: Sep. 24, 1985

[54] PROCESS AND REAGENT FOR THE DETERMINATION OF CREATININE

[75] Inventors: Winfried Albert, Pähl; Joachim Ziegenhorn, Starnberg; Joachim Siedel, Bernried; Hans-Georg Batz; Helmut Lenz, both of Tutzing; Brigitte Pautz, Herrsching, all of Fed. Rep. of Germany

[73] Assignee: Boehringer Mannheim GmbH, Mannheim-Waldhof, Fed. Rep. of Germany

[21] Appl. No.: 449,925

[22] Filed: Dec. 15, 1982

[30] Foreign Application Priority Data

Dec. 22, 1981 [DE] Fed. Rep. of Germany ....... 3150878

[51] Int. Cl.$^4$ .................... G01N 33/54; C12Q 1/34; C12N 9/96
[52] U.S. Cl. ......................... 435/7; 435/18; 435/188; 435/810; 436/512; 436/518; 436/536; 436/540; 436/543; 436/548; 436/822
[58] Field of Search .............. 435/4, 7, 18, 188, 810, 435/26; 436/512, 517, 518, 533, 534, 536, 538, 540, 543, 547, 548, 822, 823

[56] References Cited

U.S. PATENT DOCUMENTS

| 4,134,793 | 1/1979 | Terada et al. | 435/18 |
| 4,160,818 | 7/1979 | Smith et al. | 436/537 |
| 4,276,377 | 6/1981 | Goodhue et al. | 435/18 |

FOREIGN PATENT DOCUMENTS

| 73514 | 3/1983 | European Pat. Off. | 435/7 |
| WO82/04323 | 12/1982 | PCT Int'l Appl. | 435/7 |

Primary Examiner—Esther M. Kepplinger
Attorney, Agent, or Firm—Felfe & Lynch

[57] ABSTRACT

The present invention provides a process for the immunological determination of creatinine, wherein creatinine is converted into 1-methylhydantoin, the 1-methylhydantoin formed is incubated in an aqueous medium with antibodies which are directed against a conjugate of a first hydantoin derivative of the general formula:

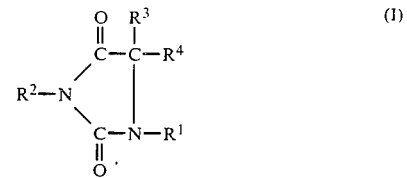

in which $R^1$, $R^2$, $R^3$ and $R^4$, which can be the same or different, are hydrogen atoms, alkyl radicals containing up to 3 carbon atoms or phenyl radicals, with a first hapten carrier substance suitable for antibody formation, reacted with a conjugate of a second hydantoin derivative of general formula (I) with a second hapten carrier substance, one of the components antibody and conjugate being present in the solid phase or in dissolved form and the other component being present in dissolved form, and the inhibition of the binding reaction between the antibodies and the hydantoin conjugate with the second hapten carrier substance is measured.

The present invention also provides a reagent for the immunological determination of creatinine, wherein it contains creatinine iminohydrolase, antibodies against a conjugate of a hydantoin of the general formula:

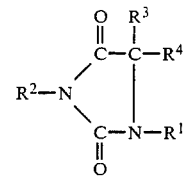

in which $R^1$, $R^2$, $R^3$ and $R^4$, which can be the same or different, are hydrogen atoms, alkyl radicals containing up to 3 carbon atoms or phenyl radicals, with a first hapten carrier substance, a conjugate of a hydantoin of general formula (I) with a second hapten carrier substance which does not cross-react substantially with the first hapten carrier substance and a buffer substance.

20 Claims, 2 Drawing Figures

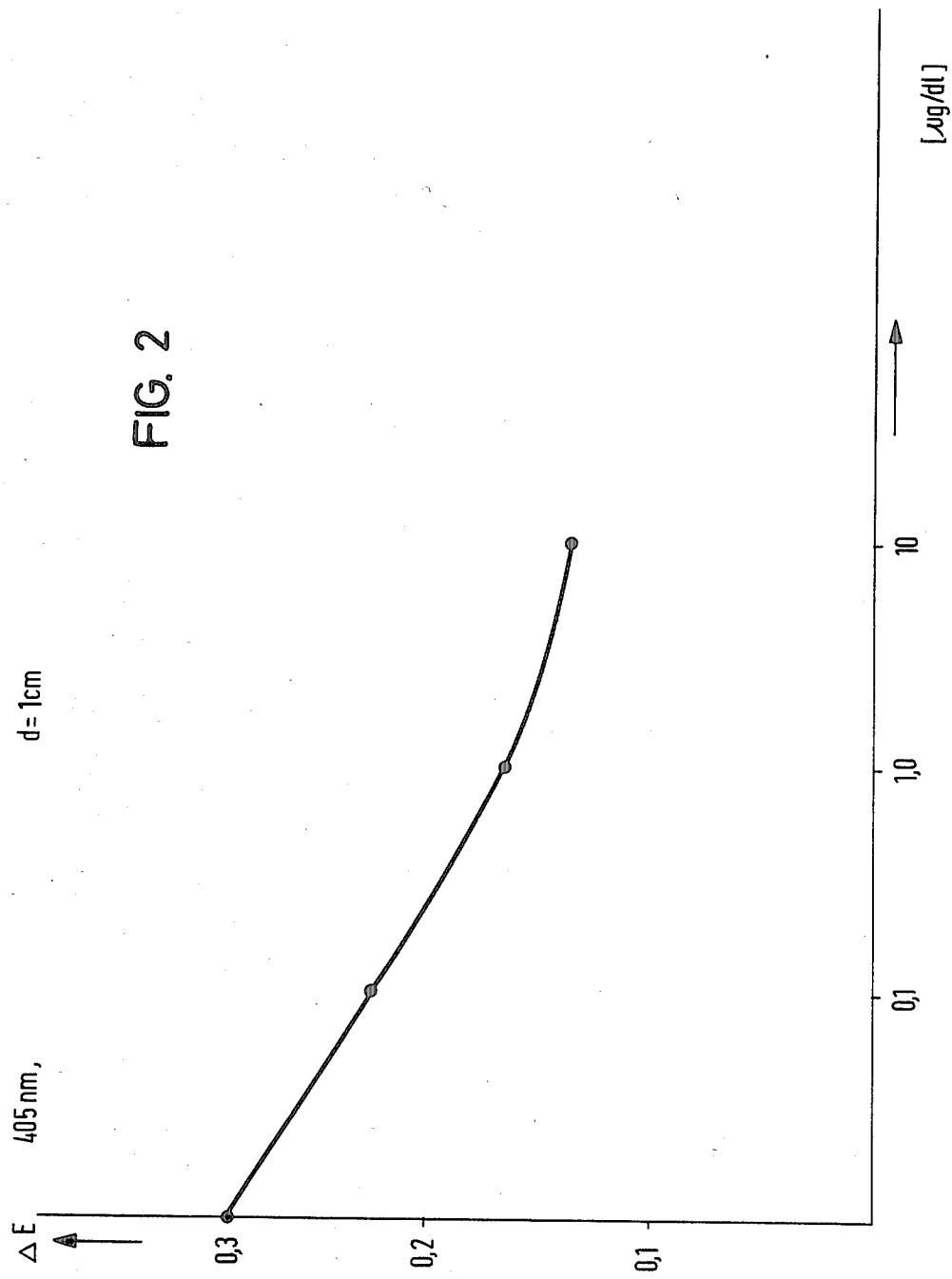

PROCESS AND REAGENT FOR THE DETERMINATION OF CREATININE

The present invention is concerned with a process for the determination of creatinine, which process has an immunological basis, and with a reagent for carrying out this process.

In clinical chemistry, the determination of creatinine is one of the most important methods for the diagnosis of kidney function. In comparison with the determination of urea, it has the decisive advantage that the concentration of creatinine in serum remains practically uninfluenced by the manner of nutrition, especially the ingestion of protein-rich foodstuffs.

However, in comparison with urea, the concentration of creatinine in serum in the decisive range (upper limit of the normal values 1.10 mg./dl in men and 9.90 mg./dl. in women) is extremely low. Therefore, the sensitivity and specificity of the creatinine test must satisfy high requirements.

Because of the importance of the creatinine test as standard method of investigation in the clinical laboratory, this should, at the same time, also be capable of being carried out with the smallest expenditure of labour and be especially suitable for use in automatic analysers.

The previously most commonly used method for the determination of creatinine depends upon the colour reaction, found by M. Jaffé, of creatinine with picric acid in an alkaline medium. After acidic deproteinisation of the sample, for example with trichloroacetic acid or picric acid, followed by the addition of picric acid and alkalisation, a red coloration develops in the supernatant, which is measured photometrically. However, this per se simple reaction suffers from a number of serious disadvantages.

It has been found that the Jaffé reaction is influenced by more than 50 substances which are also chromogenic (see Clin. Chem., 26, 1119–1126/1980) and especially by components which occur naturally in the serum, such as glucose, pyruvate, acetoacetate and acetone, so that the test is not specific for creatinine. These "non-creatinine chromogens" are especially disturbing in the case of low creatinine concentrations (<1 mg./dl.), which results in a limitation of the lower limit of detection for creatinine ("creatinine blind" range).

Slight displacements of the pH value in the reaction medium also result in a change of the depth of the colour. Finally, the use of, in some cases, caustic or poisonous reagents represents a source or danger in handling. A series of modifications of the Jaffé reaction admittedly improve the precision and the ease of carrying out without, however, completely overcoming these principle disadvantages.

According to a further known method, creatinine is converted, by the addition of o-nitrobenzaldehyde, into methylguanidine, which is then determined by the Sakaguchi reaction. A colour reaction between creatinine and potassium mercury thiocyanate is also known. However, both methods have proved to be unsuitable for use in a clinical laboratory.

It is also known to avoid disturbances by non-specific chromogens by combining the Jaffé reaction with enzymatic partial steps. In this case, the colour obtained by the Jaffé reaction with the serum sample before and after treatment with creatinine amidohydrolase/creatinine kinase/ATP is determined and the creatinine content is calculated from the difference between the extinctions (see Arch. Pharm., 3, 893–896/1980). This method is admittedly specific but it is laborious to carry out and can only be automated with difficulty.

Processes for the determination of creatinine are also known in which ammonia liberated from creatinine by the action of creatinine iminohydrolase is determined, either with ammonia-selective electrodes (see Anal. Chem., 46, 246–249/1976) or fluorimetrically via NADH consumption in a subsequent glutamate dehydrogenase reaction (see Clin. Chim. Acta, 100, 21–23/1980). However, because of the possible presence of comparatively large amounts of free ammonia in the sample material, it appears to be questionable whether such measurements can be carried out sufficiently free from disturbances and thus can find use in routine diagnosis.

Recently, a completely enzymatic creatinine test has been described in which creatinine is converted into creatine, the latter is reacted with ATP to give creatine phosphate and the ADP thereby formed is measured photometrically in a coupled reaction with pyruvate kinase and lactate dehydrogenase (LDH) via the decrease of the NADH content in the reaction solution (see Scand. J. clin. Lab. Invest., Suppl. 29, 126/1972).

This method does not require a deproteinisation of the serum sample and is specific for creatinine. However, because of the relatively low measurement signal, even in the case of the use of comparatively large volumes of sample, the sensitivity of the test in the low ranges of creatinine concentration is limited; furthermore, the necessity of having to carry out a blank determination makes the use of the method in automatic analysers very difficult.

Therefore, there is a need for a simple and automatable, simultaneously very specific and, for the above-mentioned reasons, very sensitive test for creatinine, especially in the concentration range of <1 mg./dl. ("creatinine blind" range).

The present invention solves this problem by an immunological process for the determination of creatinine, in which creatinine from a sample is first converted into 1-methylhydantoin, preferably enzymatically, for example with the help of creatinine iminohydrolase (EC 3.5.4.21), and, by means of the resultant 1-methylhydantoin, the binding reaction between a conjugate of a hydantoin derivative of the general formula:

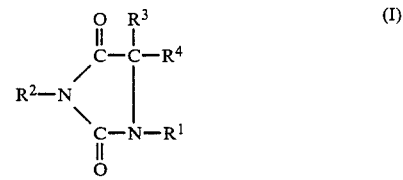

in which $R^1$, $R^2$, $R^3$ and $R^4$, which can be the same or different, are hydrogen atoms, alkyl radicals containing up to 3 carbon atoms or phenyl radicals, with a hapten carrier substance and against a conjugate of a further hydantoin derivative of general formula (I) with the same or preferably with a different hapten carrier substance directed antibodies, for example in the form of an antiserum or of an immunoglobulin fraction obtained therefrom, is inhibited in a concentration-dependent manner.

According to a preferred embodiment, not only for the binding inhibition test but also for obtaining the antibodies, use is made of conjugates of hapten carrier substances with 1-methylhydantoin ($R^1=CH_3$, $R^{2-4}=H$).

The conversion of the creatinine into 1-methylhydantoin is preferably carried out in aqueous solution before or during the incubation with the antibodies.

The binding inhibition between antibodies and hydantoin conjugate is the stronger, the more creatinine and thus the more 1-methylhydantoin is added to the antibodies before mixing with the hydantoin conjugate. The inhibition effect is already very strongly marked even in a concentration range of creatinine in the sample solution to be measured of less than 1 mg./dl., i.e. in the range in which the usefulness of the known methods of determining creatinine is already very limited.

Although there has long been a need for a simple and specific, improved method for the determination of creatinine, especially in the low concentration range, and although immunological test processes have been known for 40 years, it has hitherto not been possible to find an immunological method of determination for creatinine.

This may, inter alia, be due to the fact that creatinine is a substance which is widely distributed in the bodies of all organisms which form antibodies but which itself cannot initiate an antibody formation and, because of the low molecular size and the comparatively high serum concentration, it was not to have been expected that even a conjugate of creatinine with a hapten carrier substance could bring about the formation of antibodies which do not cross-react with compounds which are structurally closely related to creatinine, such as creatine, and thus would provide a basis for a specific method for the determination of creatinine.

The present invention overcomes this problem in that, from the creatinine, there is first formed, in an "estranging reaction", a hydantoin which itself is admittedly also a low molecular weight compound but is also a compound which is foreign to the body, against which, with appropriate hydantoin conjugates, especially with 1-methylhydantoin-hapten carrier substance conjugates, antibodies can be produced which, surprisingly, are so specific that they do not even cross-react to a significant extent with compounds normally present in the body, the important structural characteristics of which are common with those of hydantoin, for example creatinine, creatine and urea, and which, therefore, with the help of the above-mentioned "estranging reaction", are suitable for the basis of a specific and sensitive creatinine test.

As hapten carrier substances suitable for the antibody formation, there can be used those materials which are known for this purpose in immunology, for example proteins, polysaccharides, lipopolysaccharides, latex particles, active charcoal, polylysine and viruses. Examples thereof are, in principle, all foreign proteins which do not occur in the host animal used for the antibody formation, such as serum albumins of varying origin, keyhole lymphocyanines, (lipo)-polysaccharides, agarose, active charcoal and viruses. Examples of other known carrier substances for haptens are given in "The Handbook of Experimental Immunology", pub. Blackwell Scientific Publications, 3rd edition (1978), pp. 1–11. Appropriate methods for the linking of carrier substance and hapten are also given therein. Preferred hapten carrier substances in the scope of the present invention include serum albumins of varying origin, for example bovine and human serum albumin and the like, and β-galactosidase, as well as edestin.

If the conjugate used for the antibody formation contains the same hapten carrier substance as the conjugate used in the binding inhibition test, then, in this case, cross-reactions against the hapten carrier substance in the test can be selectively superimposed in that, before the determination of the actually interesting binding reaction with the hapten, the hapten carrier substance is added to the antibody fraction in the concentration necessary for the precipitation of the antibodies directed against the hapten carrier substance, whereby, in the case of carrying out the test via the determination of turbidity formation (TINIA, NINIA), the precipitates resulting by the cross-reaction of the hydantoin-conjugate antibodies with the hapten carrier substances are first removed, for example by centrifuging or filtration.

The hydantoin conjugates used for the immunisation or in the binding inhibition test are preferably prepared by binding the hydantoin to an aliphatic or araliphatic carboxylic acid and then the carboxyl group of the part originating from the carboxylic acid is attached to the hapten carrier substance. Fatty acids containing at least 2 carbon atoms and preferably 4 to 16 carbon atoms, as well as aromatic carboxylic acids with alkyl side chains, have proved to be useful for this purpose. Benzoic acid derivatives with an alkyl radical containing up to 4 carbon atoms on the aromatic ring have proved to be especially useful. Typical examples include methylbenzoic acid, ethylbenzoic acid and propylbenzoic acid. The oligomers of these araliphatic carboxylic acids, such as methyl benzoate-methylbenzoic acid, can also be used.

The binding between the hydantoin, which is here to be regarded immunologically as a hapten, and the carboxylic acid can be produced by known methods, using activated carboxylic acid derivatives. It is preferred to use halogenated carboxylic acids, especially ω-bromocarboxylic acids, in an aqueous alcoholic medium or, in the case of the corresponding halogenated carboxylic acid esters, in an anhydrous medium with subsequent saponification. The best results have been obtained with the ω-bromocarboxylic acid esters, with subsequent saponification, yields of up to 50% having been obtained. In an aqueous alcoholic medium, the reaction with the hydantoin takes place at an elevated temperature and preferably at the boiling point. If carboxylic acid esters are used, then the solvent used is preferably a polar organic compound, for example dimethylformamide, formamide, tetrahydrofuran or the like. The reaction is preferably carried out using the sodium salt of the hydantoin, which is obtained by reaction with methanolate. The saponification of the product can be carried out by gentle warming in an aqueous alkaline medium. Apart from coupling via the unsubstituted nitrogen in the 3-position of the hydantoin, coupling can also take place via the carbon atom in the 5-position ($R^3$ and $R^4=H$) by diazotisation with p-benzoic acid diazonium salt. For the immunisation, as well as in the binding inhibition test, it is preferable to use hydantoin conjugates bridged via the nitrogen atom in the 3-position.

The coupling with the hapten carrier substance is preferably carried out in an aqueous organic medium in the presence of an amine and of a chloroformic acid ester or by the preparation of the hydroxysuccinimide ester of the carboxylic acid and subsequent reaction of this ester with proteins or other carriers at a pH of from 7 to 9. Water/dioxan has proved to be especially useful as reaction medium.

The hydantoin conjugates thus obtained are used as immunogens for the antiserum formation or directly in the binding inhibition test.

For the antiserum formation, they are administered to the selected animal species using methods known in the art. The immunogen is preferably used together with Freund's adjuvant for strengthening the immune response.

For the antibody formation, there can, in general, be used all living creatures which form antibodies, sheep being preferably used. Monoclonal antibodies, such as are obtainable from cell cultures, can also be employed.

By the term "antibodies", in the scope of the present invention there are to be understood not only purified antibodies but also antisera, immunoglobulin fractions obtained from the latter, as well as antibody fragments, such as $F(ab_2)$, Fab and Fv fragments.

The inhibiting action of the 1-methylhydantoin on the binding reaction between hydantoin conjugate and hydantoin-conjugate antibodies can be measured directly by known immunological methods. By way of example, mention is made of the methods using marked antibodies or antigens, such as RIA and EIA, the latter with the ELISA and EMIT embodiments, the turbidimetric measurement of the inhibition of the immunoprecipitation between conjugate and antibody (TINIA principle) and the corresponding nephelometric methods (NINIA principle) and the like.

Furthermore, use can be made of the agglutination inhibition test (PACIA=particle counting immunoassay) and complement-bonding reactions. These methods are all well known in the art and do not need to be described here in more detail. Merely by way of example, for the EIA embodiment, reference is here made to Clin. Chim. Acta, 81, 1–36/1977 and J. Clin. Chem. Clin. Biochem., 18, 197–208/1980.

In the case of enzyme marking, mention is made of the enzymes which have been successfully used for this purpose, for example β-galactosidase, peroxidase, alkaline phosphatase, glucose oxidase, glucose-6-phosphate dehydrogenase and luciferase. In the case of coenzyme marking, there can be used for example NAD or NADP in either the oxidised or reduced state. Not only the antibody but also the hapten can be marked.

A preferred method from among the above-mentioned methods consists in that the inhibition of the binding reaction is determined by turbidimetric measurement of the immunoprecipitation in a predetermined period of time.

Another preferred method consists in that the inhibition of the binding reaction is determined by back titration of non-bound hapten carrier substance-hydantoin conjugate with marked antibodies, especially preferably with enzyme-marked antibodies, and measurement of the bound or non-bound part of the marked substance. For this purpose, there can be used, for example, the marking with radioactive substances (RIA), enzymes or co-enzymes (EIA), fluoroescence (FIA) and spin marking (cf. Nature New Biology, 236, 93–94/1972). As marked antibodies, there can also be used marked antiantibodies (double antibody method).

The present invention also provides a reagent for the immunological determination of creatinine, which contains creatinine iminohydrolase, antibodies against a conjugate of a hydantoin, preferably of 1-methylhydantoin, with a first hapten carrier substance, a conjugate of a hydantoin, preferably of 1-methylhydantoin, with a second hapten carrier substance which conjugate does not show substantial immunological cross-reactivity with the antibody of the first hapten carrier substance, and a buffer substance.

The reagent according to the present invention can also contain a substance which promotes the immunoprecipitation. Especially preferred for this purpose is polyethylene glycol, alone or optionally together with a surface-active substance. As polyethylene glycol, there can be used one with a molecular weight of from 200 to 20,000 and preferably with a molecular weight of 6000±2000. Appropriate concentrations of the polyethylene glycol in the reagent are from 0 to 8% and preferably from 1 to 4%.

With regard to the antibody component and the marking used, the statements made above apply correspondingly for the reagent according to the present invention.

According to the present invention, for the turbidimetric method of determination, a reagent is preferred which contains 0.05 to 100 U/ml. creatinine iminohydrolase, 0.5 to 500 μg./ml. of conjugate of 1-methylhydantoin and human or bovine albumin, linked via an araliphatic carboxylic acid, such as p-methylbenzoic acid, in the molar ratio of 1-methylhydantoin: serum albumin of 2:1 to 30:1, antibodies against a conjugate of 1-methylhydantoin with edestin, linked via an aliphatic carboxylic acid, such as butyric acid, in a mole ratio of 0.1 to 10, referred to the hapten conjugate binding sites and 0 to 8% of polyethylene glycol, as well as 0.05 to 1 mole/liter of buffer substance of pH 4 to 10.

For the EMIT method, the reagent according to the present invention preferably contains $10^{-4}$ to $10^{-14}$ mole/liter of antibody against 1-methylhydantoin-hapten carrier substance conjugate, referred to active receptor sites $10^{-4}$ to $10^{-14}$ mole/liter 1-methylhydantoin-malate dehydrogenase conjugate, 0.05 to 100 U/ml. creatinine iminohydralase, 0.05 to 50 mMole/liter oxaloacetic acid, 5 to 200 mMole/liter phosphate buffer (pH 6 to 8.5) and 0.05 to 0.4 mMole/liter NADH.

As buffer substances, according to the present invention there can be used all buffers which are known to be effective in the pH range of from 4 to 10 and preferably of from 6 to 9. The buffer concentration in the dissovled reagent should be from 0.005 to 1.0 mole/liter and preferably from 0.01 to 0.2 mole/liter, the range of from 0.03 to 0.07 mole/liter being especially preferred.

The antibody concentration in the test is preferably from about $10^{-4}$ to $10^{-14}$ mole/liter and more preferably from $10^{-6}$ to $10^{-12}$ mole/liter, mole/liter being understood to refer to active receptor sites.

For carrying out the process according to the present invention, the solution to be analysed can be mixed directly with the reagent. If the creatinine is present in high concentrations, the sample is preferably previously diluted with water.

In general, the determination can be carried out at a temperature of from 10° to 50° C. and preferably of from 15° to 40° C.

The hydantoin conjugate can be prepared according to known methods, for example according to the mixed anhydride method described in J. Biol. Chem., 228, 713–727/1957. The same applies to the marking with an enzyme.

The following Examples are given for the purpose of illustrating the present invention. The abbreviations used therein have the following meanings:
BSA—bovine serum albumin
HSA—human serum albumin
RIA—radioimmunoassay
EMIT—enzyme multiplied immunoassay technique
ELISA—enzyme linked immunosorbent assay
TINIA—turbidity inhibition immunoassay
NINIA—nephelometric inhibition immunoassay
CB—covering buffer
IB—incubation buffer
Tween®20—polyoxyethylene sorbitan monolaurate
DMF—dimethylformamide
WB—washing buffer
SB—substrate buffer
PNPP-Na—sodium p-nitrophenyl phosphate
AT—ambient temperature
AP—alkaline phosphatase
AP-TC—alkaline phosphatase test combination
Tinaquant-FN buffer—Na.K phosphate 66 mMole/liter (pH 8.0), EDTA 10 mMole/liter, Brij-35® 0.4%, $NaN_3$ 0.1%, polyethylene glycol 6000 3.0%
EIA—enzyme immunoassay (A) Preparation of the hydantoin conjugate 11.4 g. (100 mMole) 1-Methylhydantion are dissolved in hot anhydrous methanol and mixed with an equivalent amount of sodium methanolate. The methanol is thereafter distilled off and the residue remaining behind is dried in a vacuum and subsequently taken up in 200 ml. DMF. It is then heated to 80° to 100° C. To this solution are added slowly, while stirring, either 120 mMole/liter ethyl γ-bromobutyrate or p-bromoethylbenzoic acid. Thereafter, stirring is continued for 5 hours at 100° C., followed by cooling, whereafter the sodium bromide formed is filtered off. The filtrate is evaporated and the residue is taken up in 100 ml. isopropanol. Thereafter, freshly precipitated sodium bromide is filtered off. The filtrate is concentrated to one quarter of its volume and cooled to 4° C., a white substance thereby crystallising out. The crystallisate is recrystallised from water/methanol (1:1 v/v). The resultant ester is saponified with 1N aqueous sodium hydroxide solution.

The free acid is recrystallised from isopropanol.
The following compounds are thereby obtained:
1. 1-methyl-3-carboxybutyrylhydantoin; m.p. 102°-104° C.; yield 61% of theory
2. 1-methyl-3-(p-carboxyphenyl)-methylhydantoin; m.p. 167°-170° C.; yield 67% of theory.

For coupling to bovine serum albumin, 3.6 g. of bovine serum albumin are dissolved in 250 ml. water/dioxan (1:1 v/v), 5.6 ml. 1N aqueous sodium hydroxide solution are added thereto, whereby dissolving takes place, and the solution obtained is subsequently cooled to 4° C. To this solution is added a solution of 1.7 g. 1-methyl-3-(p-carboxyphenyl)-methylhydantoin, 1.7 ml. tributylamine and 0.95 ml. isobutyl chloroformate in 60 ml. dioxan and 3 ml. DMF. The reaction mixture is stirred for 24 hours at 4° C., then dialysed for 36 hours against flowing, desalinated water, whereafter the solution is lyophilised.

For coupling with edestin, the above procedure is used except that, instead of bovine serum albumin, use is made of edestin and instead of 1-methyl-3-(p-carboxyphenyl)-methylhydantoin, use is made of 1-methyl-3-carboxybutyrylhydantoin.

(B) Preparation of the antiserum

The immunisation of the animals used for the production of the antiserum is carried out as follows:
Animal species: sheep.
Immunogen: 1-methyl-3-carboxybutyrylhydantoin-edestin conjugate.

| | Immunisation scheme: | | |
|---|---|---|---|
| day | administration | amount of immunogen | Freund's adjuvant emulsified with |
| 0 | intradermal | 1 mg. | + |
| 7 | intramuscular | 1 mg. | + |
| 14 | subcutaneous | 1 mg. | + |
| 30 | intramuscular | 1 mg. | + |
| 60 | subcutaneous | 1 mg. | + |
| etc. | subcutaneous | 1 mg. | + |

1. Sample bleeding: day 45.

(C) Working up of the antiserum

Sheep antiserum is mixed at ambient temperature with 1% "Aerosil" (amorphous silicic acid), stirred for about 2 hours, centrifuged off and the precipitate discarded.

To the supernatant there is slowly added solid ammonium sulphate up to 1.8 mole/liter and the mixture then stirred for several hours at 4° C. The mixture is centrifuged off and the supernatant is discarded. The precipitate is taken up to 75% of the initial volume of buffer solution (50 mMole/liter potassium phosphate, pH 7.0; 100 mMole/liter sodium chloride and 0.05% sodium azide), then dialysed for about 24 hours against 0.15 mole/liter sodium chloride and subsequently centrifuged off, if necessary.

The supernatant is then dialysed for about 8 to 10 hours against 3 mMole/liter hydrochloric acid, with a change of the dialysis solution (1:100 volume ratio). Precipitates formed are centrifuged off and discarded.

There subsequently takes place a back-dialysis against 10 mMole/liter potassium phosphate (pH 7.0), 150 mMole/liter sodium chloride for about 12 hours (volume ratio 1:100). Precipitates formed are centrifuged off and discarded.

EXAMPLE 1

TINIA principle (a) Reagents creatinine solutions: concentrations of from 0.2 to 1000 mg./dl. Tinaquant-FN buffer
creatinine iminohydrolase
antiserum against 1-methyl-3-carboxybutyrylhydantoinedestin conjugate, diluted 1:5 with Tinaquant-FN buffer and freed from turbidity by centrifuging
1-methyl-3-(p-carboxyphenyl)-methylhydantoin-BSA conjugate (2 mg./ml. Tinaquant-FN buffer).

(b) Test batch

Into cuvettes (d=1 cm.) there are pipetted 1 ml. amounts of diluted antiserum, containing 10 U creatinine iminohydrolase, 10 μl. of creatinine solutions of differing concentrations or 10 μl. Tinaquant-FN buffer for use as a blank and the cuvettes then incubated for 10 minutes at 25° C.

Subsequently, 10 μl. of the methylhydantoin-BSA conjugate are pipetted into each cuvette and the increase of the turbidity is measured photometrically at 366 nm after the addition of the methylhydantoin-BSA conjugate ($E_1$ before the start, $E_2$ 5 minutes after the start). FIG. 1 of the accompanying drawings shows a calibration curve obtained in this manner, in which the extinction difference is plotted against the creatinine concentration.

EXAMPLE 2

ELISA principle (based upon the process described in J. of Immunology, 123, 1548–1550/1979)

(a) Reagents covering buffer (CB)
 0.2 mole sodium carbonate/liter, pH 9.3–9.5
incubation buffer (IB)
 0.05 mole/liter potassium phosphate, pH 7.2
 0.1 mole/liter sodium chloride
 1% glycine
 0.05% "Tween" 20
 0.02% sodium azide
washing buffer (WB)
 0.15 mole/liter sodium chloride
 0.05% "Tween" 20
 0.02% sodium azide
substrate buffer (SB)
 AP test
 1 tablet/76 ml. buffer or
 17 mg. PNPP-Na$_2$/10 ml. buffer from 123 854
conjugate of AP with rabbit-antisheep-IgG creatinine iminohydrolase (b) Test batch Microtitre plates are covered with 200 μl. methylhydantoin-BSA conjugate (0.50 μg./ml. CB or 0.50 μg. BSA/ml. CB for the blank), incubated for about 16 hours at ambient temperature and then suction filtered. 300 μl. IB are then added thereto, incubated for 1 hour, again suction filtered, thereafter 300 μl. wash buffer added thereto and again suction filtered. Subsequently, there takes place the loading with methylhydantoin antiserum. For this purpose, 1000 μl. antiserum (diluted 1:200 to 1:2000 with IB), containing 10 U/ml. creatinine iminohydrolase, are incubated with 10 μl. creatinine sample or with 10 μl. IB (for the blank) for 30 minutes at ambient temperature, then 200 μl. of the so obtained antiserum dilution are applied to the coated microtitre plate, which is closed and left to stand for 60 minutes (plastics bag), suction filtered, 300 μl. WB added thereto and again suction filtered.

For the conjugate covering, 200 μl. rabbit-antisheep IgG-AP conjugate containing 150 mU AP/ml. IB are applied to the treated microplates, maintained for 2 hours at 37° C., then suction filtered and, in each case, washed with 300 μl. WB.

For the colour development, 200 μl. substrate buffer are added thereto and the mixture is incubated for 30 to 60 minutes. The evaluation takes place in that 150 μl. test solution from the microtitre plates are measured with 500 μl. sodium hydroxide solution (0.1 mole/liter) at 405 nm against the blank. FIG. 2 of the accompanying drawings shows a calibration curve obtained with differing creatinine concentrations.

EXAMPLE 3

EMIT principle 2.00 ml. 50 mMole/liter potassium phosphate buffer (pH 7.5) with 10 U/ml. creatinine iminohydrolase are mixed with:
 0.02 ml. sample (or water for the blank)
 1.00 ml. 0.7 mMole/liter oxalacetic acid in buffer solution (50 mMole/liter phosphate, pH 7.5)
 0.01 ml. $4 \times 10^{-7}$ mole/liter methylhydantoin-edestin antiserum (binding site concentration)
 0.04 ml. $1.4 \times 10^{-2}$ mole/liter NADH After incubating for 20 to 30 minutes at 30° C., there is added thereto 0.05 ml. $1 \times 10^{-8}$ mole/liter 1-methylhydantoin-malate dehydrogenase conjugate and the enzyme activity is measured as $\Delta E$/min. spectrophotometrically at 340 nm and 30° C.

We claim:

1. Process for the immunological determination of creatinine, wherein creatinine is converted into 1-methylhydantoin, the 1-methylhydantoin formed is incubated in an aqueous medium with antibodies which are directed against a conjugate consisting of a first hydantoin derivative of the general formula:

$$\begin{array}{c} \text{O} \quad R^3 \\ \| \quad | \\ \text{C} - \text{C} - R^4 \\ R^2 - N \\ \diagdown \\ \text{C} - N - R^1 \\ \| \\ \text{O} \end{array} \quad (I)$$

in which $R^1$, $R^2$, $R^3$ and $R^4$, which can be the same or different, are hydrogen atoms, alkyl radicals containing up to 3 carbon atoms or phenyl radicals, covalently linked to a first hapten carrier substance suitable for antibody formation, reacted with a second conjugate consisting of a second hydantoin derivative of general formula (I) covalently linked to a second hapten carrier substance, either one of the incubation components antibody or second hydantoin derivative-second hapten carrier substance conjugate being adsorbed on a solid phase and the other component being present in dissolved form, or both incubation components being present in dissolved form, and the inhibition of the binding reaction between the antibodies and the second hydantoin derivative-second hapten carrier substance conjugate as mediated by the free 1-methyl hydantoin formed from creatinine, is measured.

2. Process according to claim 1, wherein the conversion of the creatinine into 1-methylhydantoin is carried out in aqueous solution before or during the incubation with the antibodies and the creatinine is converted enzymatically into 1-methylhydantoin.

3. Process according to claim 1, wherein the first and second hydantoin derivatives are methyl-hydantoin (I; $R^1 = CH_3$; $R^2$-$R^4 = H$).

4. Process according to claim 1, wherein each of the first and second hapten carrier substance is a protein, a polysaccharide, a lipopolysaccharide, latex particles, active charcoal, polylysine or viruses.

5. Process according to claim 4, wherein the protein used is human serum albumin, bovine serum albumin, β-galactosidase or edestin.

6. Process according to claim 4 or 5, wherein the second hapten carrier substance is human serum albumin, bovine serum albumin, β-galactosidase or latex.

7. Process according to claim 1, wherein the hydantoin derivatives are covalently linked to the hapten carrier substance via aliphatic or araliphatic carboxylic acids as bridge members.

8. Process according to claim 7, wherein conjugates are used, the carboxylic acid bridge of which contains at least 2 carbon atoms.

9. Process according to claim 7, wherein conjugates are used which, as bridge member, contain an alkylphenylcarboxylic acid or an oligomer thereof.

10. Process according to claim 1, wherein conjugates are used which, per molecule of hapten carrier substance, contain 1 to 50 molecules of hydantoin.

11. Process according to claim 1, wherein the antibodies are used in the form of an antiserum or of an immunoglobulin fraction obtained therefrom or of monoclonal antibodies or as antibody fragments.

12. Process according to claim 1, wherein the inhibition of the binding reaction is determined by nephelometric or turbidimetric measurement of the immunoprecipitation in a predetermined period of time.

13. Process according to claim 1, wherein the inhibition of the binding reaction of non-bound hapten carrier substance-hydantoin conjugate is determined with marked antibodies and measurement of the bound or non-bound portion of the marked substance.

14. Process according to claim 1, wherein sheep antibodies are used.

15. Reagent for the immunological determination of creatinine, wherein it contains creatinine iminohydrolase, antibodies against a conjugate consisting of a hydantoin of the general formula:

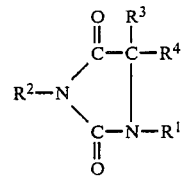

in which $R^1$, $R^2$, $R^3$ and $R^4$, which can be the same or different, are hydrogen atoms, alkyl radicals containing up to 3 carbon atoms or phenyl radicals covalently linked to a first hapten carrier substance, a conjugate consisting of a hydantoin of general formula (I) covalently linked to a second hapten carrier substance, which conjugate does not show a substantial immunological cross-reactivity with the antibody of the first hapten carrier substance and a buffer substance.

16. Reagent according to claim 15, wherein the hydantoin is 1-methylhydantoin.

17. Reagent according to claim 15, wherein the antibodies are present as antiserum, immunoglobulin fraction, antibody fragments or monoclonal antibodies.

18. Reagent according to claim 17, wherein the antibodies are marked.

19. Reagent according to claim 15 comprising, 0.05 to 100 U/ml. creatinine iminohydrolase, 0.5 to 500 μg./ml. conjugate of 1-methylhydantoin and serum albumin in a molar ratio of 1-methylhydantoin:serum albumin of 2:1 to 30:1, antibody-1-methylhydantoin conjugate in a mole ratio of 0.1 to 10, referred to the hapten binding site concentration, 0.1 to 8% by weight of polyethylene glycol and a buffer substance with an ionic strength of 0.03 to 0.4 and a pH of 4 to 10.

20. Reagent according to claim 15 comprising, 0.05 to 100 U/ml. creatinine iminohydrolase, $10^{-4}$ to $10^{-14}$ mole/liter of antibodies against 1-methylhydantoin-hapten carrier substance conjugate, referred to the active hapten receptor points, $10^{-4}$ to $10^{-14}$ mole/liter 1-methylhydantoin-malate dehydrogenase conjugate, 0.05 to 50 mMole/liter oxalacetic acid, 5 to 200 mMole/liter phosphate buffer (pH 6 to 8.5) and 0.05 to 0.4 mMole/liter NADH.

* * * * *

UNITED STATES PATENT AND TRADEMARK OFFICE
CERTIFICATE OF CORRECTION

PATENT NO. : 4,543,325
DATED : September 24, 1985
INVENTOR(S) : Winfried Albert et al It is certified that error appears in the above-identified patent and that said Letters Patent is hereby corrected as shown below:

Column 1, line 18:

"9.90 mg./dl." should be changed to read --0.90 mg./dl.--

Signed and Sealed this

First Day of April 1986

[SEAL]

Attest:

Attesting Officer

DONALD J. QUIGG

Commissioner of Patents and Trademarks